(12) United States Patent
Kramer

(10) Patent No.: US 6,894,779 B2
(45) Date of Patent: May 17, 2005

(54) APPARATUS FOR DETECTING BACK-SCATTER IN A LASER-BASED BLOOD ANALYSIS SYSTEM

(75) Inventor: Donald L. Kramer, Boca Raton, FL (US)

(73) Assignee: Coulter International Corp., Miami, FL (US)

( * ) Notice: Subject to any disclaimer, the term of this patent is extended or adjusted under 35 U.S.C. 154(b) by 64 days.

(21) Appl. No.: 10/227,004

(22) Filed: Aug. 23, 2002

(65) Prior Publication Data

US 2004/0036875 A1 Feb. 26, 2004

(51) Int. Cl.$^7$ .............................................. G01N 21/00
(52) U.S. Cl. ...................................................... 356/342
(58) Field of Search ................................. 356/335–343; 250/574, 575, 227.28; 385/114–116

(56) References Cited

U.S. PATENT DOCUMENTS

| | | | |
|---|---|---|---|
| 3,835,315 A | * 9/1974 | Gravitt, Jr. | 250/574 |
| 4,702,598 A | 10/1987 | Bohmer | |
| 4,914,310 A | * 4/1990 | Jarofski | 250/574 |
| 5,461,476 A | * 10/1995 | Fournier | 356/343 |
| 6,137,108 A | * 10/2000 | DeThomas et al. | 250/339.07 |

FOREIGN PATENT DOCUMENTS

JP          61-23947    *  1/1986

OTHER PUBLICATIONS

Eisert, W.G., "Cell Differentiation Based on Absorption and Scattering", *The Journal of Histochemistry and Cytochemistry*, vol. 27, No. 1, pp. 404–409 (1979).
Sloot, et al., "Elastic Light Scattering from Nucleated Blood Cells: Rapid Numerical Analysis", *Applied Optics*, vol. 25, No. 19, Oct. 1, 1986.
Sloot, et al., Scattering Matrix Elements of Biological Particles Measured in a Flow Through System: theory and Practice:, *Applied Optics*, vol. 28, No. 10, May 15, 1989.

* cited by examiner

*Primary Examiner*—Hoa Q. Pham
(74) *Attorney, Agent, or Firm*—Warren W. Kurz; Mitchell E. Alter

(57) ABSTRACT

A back-scatter detector for detecting light scattered backwardly (i.e., reflected) by an irradiated particle such as a blood cell comprises a plurality of optical fibers. A fiber optic holder having a centrally located opening for passing a light beam used to irradiate particles at a particle-interrogation zone serves to position the light-collecting ends at a desired position to collect back-scattered light. Preferably, the light-collecting ends of the optical fibers are positioned in a circular pattern centered about the irradiating light beam, and the respective axes of the supported portions of the optical fibers extend either parallel to the beam axis, or, more preferably, so that they converge at or near the location of the scattering source, i.e., the irradiated particle or cell. The latter configuration assures that the back-scatter light enters the fiber end substantially parallel to the fiber axis, thereby reducing optical transmission loses in the fiber.

8 Claims, 3 Drawing Sheets

APPARATUS FOR DETECTING BACK-SCATTER IN A LASER-BASED BLOOD ANALYSIS SYSTEM

CROSS REFERENCE TO RELATED APPLICATIONS

Reference is made to the following commonly assigned U.S. patent applications filed concurrently herewith in the name of Donald L. Kramer. The respective disclosures of these applications are incorporated herein by reference:

(1) U.S. application Ser. No. 10/227,003, entitled "Fiber Optic Apparatus for Detecting Light Scatter To Differentiate Blood Cells and the Like";

(2) U.S. application Ser. No. 10/227,010, entitled "Method and Apparatus for Differentiating Blood Cells Using Back-Scatter."

FIELD OF THE INVENTION

The present invention generally relates to the field of particle characterization. More particularly, it relates to improvements in apparatus for characterizing particles, specifically blood cells, on the basis of their respective back-scatter signature.

BACKGROUND OF THE INVENTION

The use of light scattering measurements as a means for differentiating various types of small particles is well known. For example, in virtually all sophisticated hematology instruments, it is common to measure the forward light scattering properties of blood cells by passing the cells, one at a time, through the interrogation zone of an optical flow cell. While in the interrogation zone, each cell is irradiated by a laser beam, and one or more photodetectors, strategically positioned forward of the interrogation zone, operate to sense the level of forward scattered radiation, often within different predetermined angular ranges. In addition to measuring forward light scatter, some hematology instruments measure side scatter as well, using a separate photodetector located laterally of the irradiated cell. These light scattering measurements are often combined with other simultaneously made measurements, e.g., axial light-loss, DC volume and/or RF conductivity measurements, to better differentiate cell types of particular interest from other cells and particulate material in the sample that have similar light-scattering properties within the measurement ranges. Having made the various parameter measurements, the instrument then produces scattergrams in which the different parameters measured are plotted against each other. Ideally, each cell type appears on these scattergrams as a tight cluster of data points, each point representing an individual cell, and each cluster being readily identifiable by a clearly identified spacing from other clusters of data points. In such case, it is a relatively simple matter to "gate" cells of one cluster from those of another cluster and to enumerate the cells of each type. This ideal, unfortunately, is sometimes difficult to realize since, for a variety of reasons, a certain (low) percentage of cells of one type invariably invade the spatial domain of cells of other types, making the differentiation of each type somewhat imprecise.

It has been suggested that multiple bundles of fiber optics, arranged in concentric rings, can be used to optically couple scattered radiation from a scatter plane to multiple photo-detectors (e.g., photomultiplier tubes and photodiodes) remotely spaced from the scatter plane. See, "Cell Differentiation Based on Absorption and Scattering" by Wolfgang G. Eisert, The Journal of Histology and Cytochemistry, Vol.27, No.1, pp404–409 (1979). As described by Eisert, optical fibers are arranged so that their respective light-collecting ends form five concentric rings centered about a centrally located light-collecting bundle of optical fibers. The respective distal ends of the individual fibers of each of the five concentric rings are optically coupled to five different photomultiplier tubes, and the distal ends of the individual fibers of the center bundle are optically coupled to a photodiode. Thus, each ring of fibers collects scattered light in a discrete angular range determined by the diameter of the fiber (or the width of the rings), the radial displacement of the fiber end relative to the beam axis (i.e., the diameter of the ring), and the axial spacing of the fiber ends from the scattering light source. The center bundle of fibers is optically aligned with the beam axis, and the other bundles, with their individual fibers being arranged in a circle, are arranged parallel to the beam axis. The center bundle of fiber optics, being positioned on the beam axis, serves to monitor the axial light loss of the beam, as occasioned by the passage of cells therethrough.

In the fiber-optic light coupler proposed by Eisert above, the respective light-collecting ends of all the fibers are disposed in a common plane that is arranged perpendicular to the optical axis of the cell-irradiating light beam. Thus, it will be appreciated that, due to the numerical aperture of the fibers, the optical coupling of scattered light into the optical fibers deteriorates as the scatter angle increases. Additionally, as the scatter angle increases, the angle of incidence between the scattered light and the fiber end increases, thereby increasing the number of internal reflections required to transmit the scattered light from one end of the fiber to the other end. This problem of coupling efficiency is exacerbated by the dramatic reduction in scatter intensity at relatively large scatter angles.

In addition to forward- and side-scatter measurements, it has been suggested that back-scatter (i.e., reflected light) measurements may prove useful in differentiating blood cell types. In a theoretical paper entitled, "Elastic Light Scattering From Nucleated Blood Cells: Rapid Numerical Analysis," by Sloot and Figdor, Applied Optics, Vol. 25, No. 19, 1 Oct. 1986, it is noted that simultaneous detection of the light-scatter intensities in the forward-, lateral-, and back-scatter directions is required to optimize the detection of different cell types in heterogeneous populations of nucleated blood cells. Here, a model is presented to calculate the light-scattering properties of nucleated blood cells which are mimicked by two concentric spheres. It is derived from the calculations presented (no actual measurements on cells were made) that the back-scatter intensity is determined by the nucleus/cytoplasm ratio and changes in the optical density of the cytoplasm and nucleus. The analysis presented strongly suggests a direct correlation between the transparency of the nucleus and the intensity of the back-scatter signal. While no hardware is disclosed in this paper for making any light-scattering measurements at all, a subsequent paper, "Scattering Matrix Elements of Biological Particles Measured in a Flow Through System: Theory and Practice" by Sloot et al., Applied Optics, Vol. 28, No. 10, 15 May 1989, alludes to the use of large surface-area scatter detectors and the need to apply "large cone integration" to account for the relatively large surfaces. This paper schematically illustrates a back-scatter detector having a central aperture through which a particle-irradiating laser beam travels before irradiating the particle. Upon striking the particle, the large surface of the back-scatter detector collects and detects back-scattered light through a large cone angle, i.e., throughout a large angular range. While large surface area detectors are advantageous from the standpoint that they produce a relatively strong signal due to their collection of light scattered over a large angular range, they are disadvantageous from a signal-to-noise standpoint. As the surface area increases, the detector is sensitive to increasing amounts of stray light, e.g. the laser light reflecting from the faces of the optical flow cell through which the back-scattered light from the cells is detected.

SUMMARY OF THE INVENTION

In view of the foregoing discussion, an object of this invention is to provide an improved apparatus for collecting back-scattered light from a blood cell or other particle (biological or otherwise) that has been irradiated by a laser beam, and for efficiently coupling such light to a photodetector remotely spaced from the collection area.

According to the invention, a back-scatter detector comprises a plurality of optical fibers, each having a light-collection end and an opposing light-discharge end. A fiber optic holder, having a centrally located opening for passing a light beam used to irradiate particles at a particle-interrogation zone, serves to position the light-collecting ends at a desired position to collect back-scattered light. The fiber optic holder is designed to support a linear portion of each fiber in the vicinity of its light collecting end so that each fiber end receives back-scattered light from irradiated particles within substantially the same angular range. Preferably, the light-collecting ends of the optical fibers are arranged in a circular pattern centered about the irradiating light beam, and the respective axes of the supported portions of the optical fibers extend either parallel to the beam axis, or, more preferably, so that they converge at or near the location of the scattering source, i.e., the irradiated particle or cell. The latter configuration assures that the back-scatter light enters the fiber end substantially parallel to the fiber axis, thereby reducing optical transmission loses in the fiber. Preferably, the fibers are supported so that the light-collecting ends are in a common plane, or, more preferably, so that they are on a spherically-concave surface having a center of curvature proximate the scattering source.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
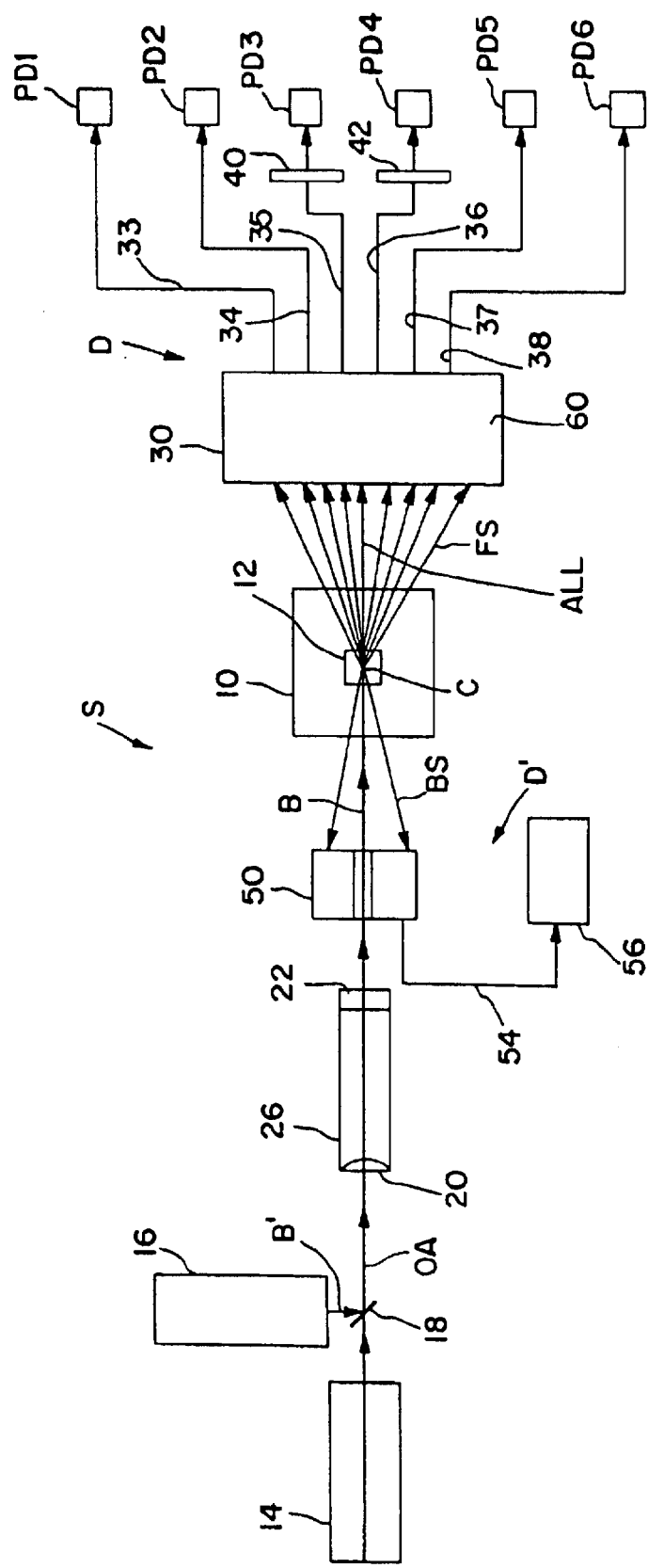
FIG. 1 is a schematic illustration of a portion of a system used to analyze blood cells and other small particles on the basis of the light-scattering signature of such cells and particles.

Referring now to the drawings, FIG. 1 schematically illustrates an electrooptical system S for detecting light scattered by small particles, e.g., blood cells, irradiated by a collimated light beam. As indicated above, systems of this general type are commonly used in hematology instruments for differentiating different types of blood cells in a liquid sample. Central to this particular system is an optical flow cell 10 having a centrally located particle-interrogation zone 12 through which a stream of individual particles of interest in suspension can be made to pass, one at a time, in a well known manner. The flow cell is optically transparent, preferably being fabricated from quartz, and the interrogation zone measures about 100×100 microns in transverse cross section. While passing through the interrogation zone, the individual particles are irradiated by a light beam B provided by a laser 14 and propagating along an optical axis OA. Preferably, a second laser 16 is used to provide a second light beam B' that becomes co-linear with beam B after striking the 45 degree, semi-transparent mirror 18. Preferably, the two beams are of different wavelength, for example, one beam being red in color, as provided, e.g., by a helium-neon laser, and the other beam being blue in color, as provided, e.g., by an argon laser. Upon passing through a small aperture formed in the light-collecting optical system comprising a back-scatter detector D' (described below), the beam(s) are brought into sharp focus at the center C of the particle-interrogation zone 12 by a pair of crossed cylindrical lens 20, 22 supported at opposite ends of a lens housing 26. When irradiated by the focused beam(s), each particle acts to scatter light in all directions according to a complex function based upon the wavelength of the irradiating light beam and certain particle characteristics, including size, refractive index, reflectivity, geometry, internal make-up, etc. Further, each irradiated particle acts to modulate the intensity of the irradiating beam(s), again depending on the physical and optical properties of the particle. Forward light scatter FS, i.e., the light scattered forwardly of the irradiated particle, as determined by the direction of propagation of the particle-irradiating beam, is detected within a plurality of different angular ranges by a forward-scatter/axial light-loss detector D. As its name suggests, detector D also operates to detect the axial light loss (ALL) in the irradiating beam(s) (sometimes referred to as "zero angle scatter") as occasioned by the passage of a particle through the beam(s). Preferably, such axial light loss is detected at different wavelengths, as determined by the respective radiant outputs of lasers 14 and 16. Back-scattered light BS, i.e., light scattered backwardly or reflected from the irradiated particles toward the irradiating source, is detected within a predetermined angular range by the above-mentioned back-scatter detector D'. The details of a preferred back-scatter detector D' are disclosed below.

Briefly, the forward-scatter/axial light loss detector D generally comprises (i) an optical fiber holder 30, (ii) a plurality of discrete fiber optic bundles 33–38 (illustrated as being six in number, though there may be more or less), and (iii) a like plurality of photodetectors PD1–PD6. The photodetectors may be conventional photomultiplier tubes, solid state devices or any combination of the two. Each fiber optic bundle preferably comprises at least three or four optical fibers and may comprise upwards of fifty fibers, depending on the pattern in which they are arranged within the fiber holder 30, and the diameter of the fibers. Each optical fiber has a light-collecting end that, in use, is positioned to collect or receive radiant energy that is to be transferred by the fiber, via multiple internal reflections, to a relatively remote location, and an opposing light-discharge end that emits the collected and transmitted light. The optical fiber holder 30 serves to position the light-collecting ends of the fibers of each bundle to form a plurality of concentric rings, one ring per bundle. Each ring serves to collect forwardly scattered light within a discrete angular range depending on the ring diameter, the fiber diameter and the axial spacing of the ring from the scattering source. The respective light discharge ends of each fiber optic bundle are optically coupled to only one of the photodetectors. Thus, the output of each photodetector represents the scattered light intensity received by the fiber optic bundle to which it is optically coupled. A pair of spectral filters 40, 42, positioned in the light path of bundles 35 and 36 serve to transmit light of one or the laser beams so as to monitor the axial light loss at two different wavelengths. Preferably, all of the individual fibers in the fiber optic bundles are the same in all respects except, perhaps, for length, which may vary slightly from bundle to bundle, depending on space constraints. Preferably, each fiber has a diameter of about 500 microns, and all fibers are made from a common optical material. Particularly preferred fibers are the SI Bare Fibers, sold by Boston Optical Fiber. Further details of the forward-scatter/axial light loss detector are described in the above-referenced U.S. patent application Ser. No. 10/227,010, filed concurrently herewith.

Figure 2A:
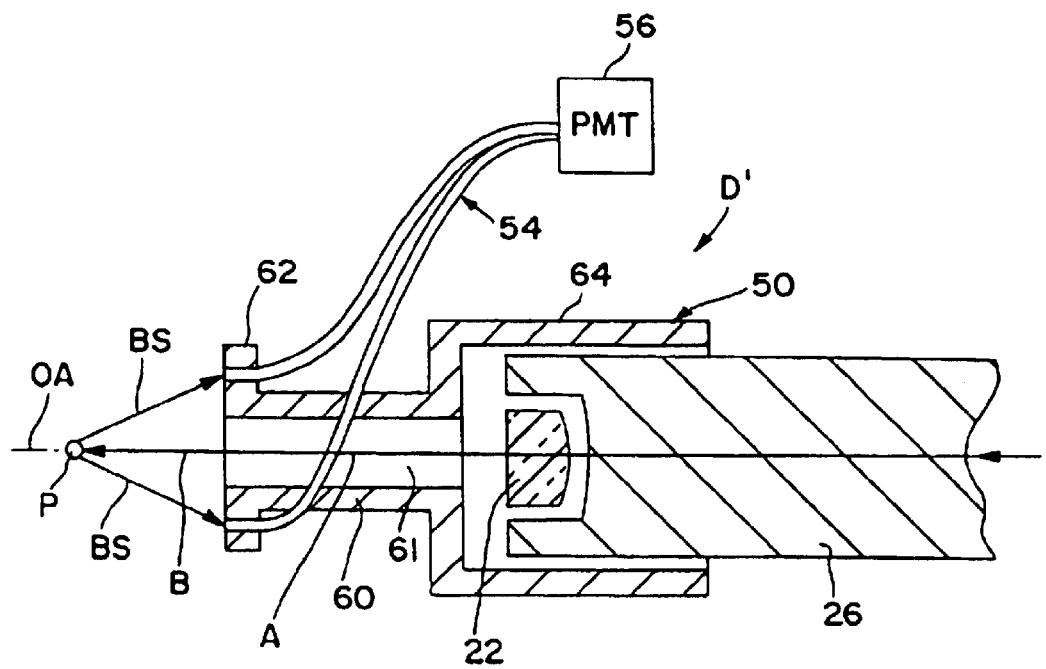
FIGS. 2A and 2B are cross-sectional and front plan views, respectively, of a back-scatter detector embodying the present invention.
Figure 2B:
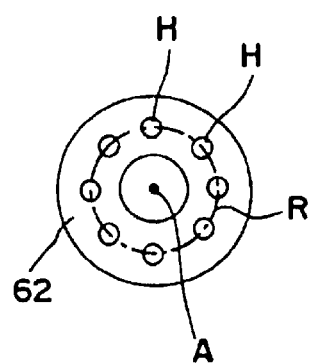

Referring additionally to FIGS. 2A and 2B, the back-scatter detector D' comprises a fiber optic holder 50, a bundle of optical fibers 54 and a photodetector 56. The optical fibers are preferably the same as those described above, and the photodetector is a conventional photomultiplier tube (PMT). The optical fiber holder 50 is preferably made of black plastic, most preferably Delrin® plastic, a product of E.I. Du Pont. Holder 50 comprises a relatively tiny central tubular portion 60 having a central bore 61 extending along its entire length. The central tubular potion 60 is provided with a circular, fiber-holding flange 62 at one end, and an enlarged tubular portion 64 at its opposing end. According to a preferred embodiment, the central tubular portion 60 has a length of about 2.5 mm., and an outside diameter of about 1.5 mm. The diameter of bore 61 is about 1.3 mm, sufficiently large to pass the particle-irradiating beam(s) B so that it can irradiate a particle P after passing through the bore. The enlarged tubular portion 64 has a length of about 4.0 mm., an outside diameter of about 3.3 mm. and an inside diameter of about 3.0 mm. The inside diameter of portion 64 is adapted to fit snugly over the end of lens housing 26, whereby the lens housing provides total support for the fiber optic holder.

As best shown in FIG. 2B, the circular flange 62 is provided with a plurality of bore holes H, each having a diameter adapted to receive and retain the light-collecting end portion of an optical fiber of the type described above; thus, each hole H has a diameter slightly exceeding the 500 micron fiber diameter. The bore holes H are arranged in a circular pattern to form a ring R centered about the central longitudinal axis A of the holder 50. Note, in use, axis A is coincident with optical axis OA. Preferably, ring R has a diameter of about 1.75 mm. Based on the anticipated spacing between the end of flange 62 (which is intended to abut the front face 10 A of the flow cell 10) and the scattering source (i.e., the center of flow cell), this ring diameter provides a nominal back-scatter angle of about 7 degrees; and the 500 micron fiber diameter provides an angular range of about 2 degrees (centered about 7 degrees). Thus, the angular range through which back-scatter is collected by the fiber optic bundle 54 is between about 6 and about 8 degrees. Due to the relatively small area of the respective light-collecting ends of the optical fibers, and the fact that each end preferably points directly at the scatter source, the fibers collect relatively little stray laser light reflecting from various sources (e.g. the faces of the optical flow cell) located between the forward-scatter detector and the back-scatter detector. Thus, through the use of fibers 56, the signal-to-noise level of photodetector 56 is maintained relatively high compared to the non-directional, large-area prior art detectors that collect, in addition to the back-scatter signal of interest, large amounts of back-scattered light from sources other than the cells of interest.

Figure 3A:
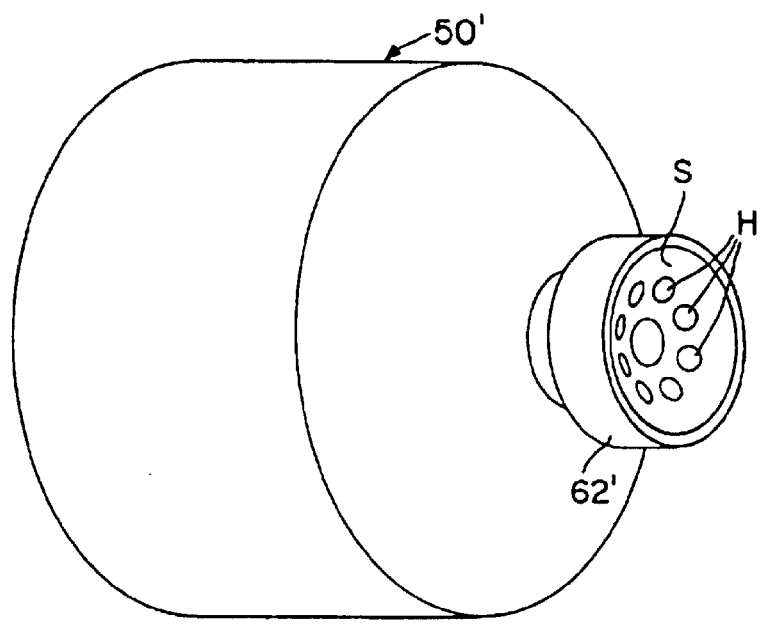
FIGS. 3A and 3B are perspective and cross-sectional illustrations, respectively, of another preferred embodiment of the invention.
Figure 3B:
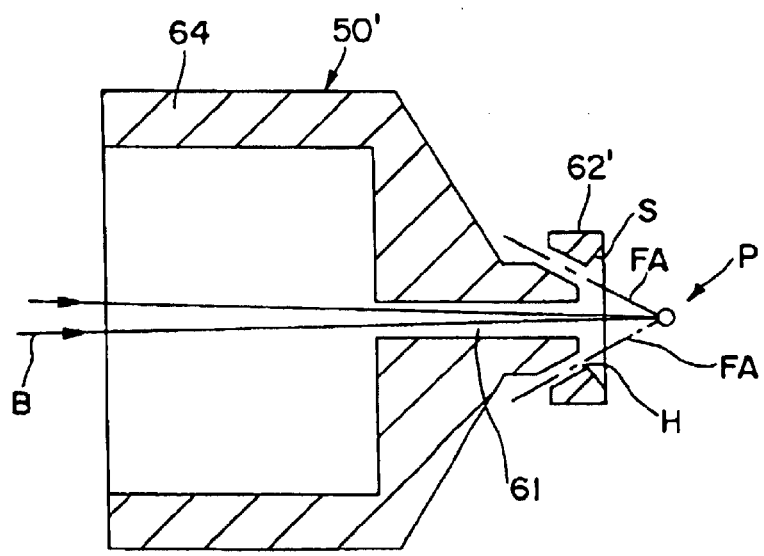

In the embodiment shown in FIG. 2A, it will be seen that the light-collecting end portions of the optical fibers are supported so that each fiber axis FA extends substantially parallel to the axis A of holder 50. In FIGS. 3A and 3B, another, more preferred, embodiment of the invention is shown in which a fiber holder 50' serves to support the fiber end portions so that their respective axes FA converge at a point P that represents the apparent position of the scattering source, i.e., the virtual position as viewed through the refractive front face of the flow cell. Here, a modified flange 62' is provided in which the fiber-containing bore holes H are formed (drilled) in a spherically-concave surface S. By this arrangement, the back-scattered light from the irradiated particle enters the light-collecting ends of the fibers from a direction that is substantially parallel to the fiber axis FA. Thus, optical losses due to multiple internal reflections within the fibers are reduced. This is especially advantageous in light of the relatively low-intensity back-scatter received from the particles.

As described in the above-referenced U.S. Patent Application entitled "Method and Apparatus for Differentiating Blood Cells Using Light Scatter," the apparatus of the invention is especially useful in differentiating various blood cells, and especially platelets, on the basis of their respective back-scatter signatures.

While the invention has been disclosed with reference to particularly preferred embodiments, it will be appreciated that various modifications can be made without departing from the spirit of the invention, and such modifications are intended to be encompassed by the ensuing claims.

What is claimed is:

1. A back-scatter detector for detecting light scattered backwardly from an individual particle or blood cell irradiated by a light beam at a particle interrogation zone within an optical flow cell of a blood cell analyzer, said back-scatter detector comprising:

(a) a photodetector;

(b) a plurality of optical fibers, each having a light-collection end, an opposing light-discharge end, and an intervening light-transport region for transmitting, by multiple internal reflections, light collected by said light-collecting end, to said light-discharge end said light-discharge end being positioned proximate a light-sensitive face of said photodetector; and (c) a fiber optic holder comprising a housing having a centrally located opening therein for passing a light beam used to irradiate particles at said particle interrogation zone, said fiber optic holder operating (i) to position the respective light-collecting ends of said optical fibers at a desired position to collect said back-scattered light, and (ii) to support linear portions of said optical fibers in the vicinity of their respectiv light-collecting ends so that the loagitudinal axes of said supported linear portions converge at or near the anticipated location of said particle-interogation zone, said housing of said optical fiber holder comprising a tubular portion adapted to engage a lens housing of a lens system adapted to focus said light beam at said interrogation zone and thereby provide support for said optical fiber holder between said lens system and said particle-interrogation zone.

2. The back-scatter detector as defined by claim 1 wherein said fiber optic holder is designed to support a linear portion of each fiber in the vicinity of its light collecting end so that each fiber end receives back-scattered light from irradiated paiticles within substantially the same angular range.

3. The back-scatter detector as defined by claim 2 wherein said light-collecting ends of said optical fibers are arranged in a circular pattern centered about said opening in said housing.

4. A back-scatter detector for detecting light scattered backwardly from an individual particle or blood cell irradiated by a focused light beam at a particle-interrogation zone of an optical flow cell comprising a blood cell analyzer, said back-scatter detector comprising:

(a) a photodetector;

(b) a plurality of optical fibers, each having a light-collection end, an opposing light-discharge end, and an intervening light-transport region for transmitting, by multiple internal reflections, light collected by said light-collecting end to said light-discharge end, said light-discharge end being positioned proximate a light-sensitive face of said photodetector; and (c) a fiber optic holder comprising a housing having an opening therein for passing said light beam used to irradiate particles at said particle-interrogation zone, said fiber optic holder operating to position the respective light-collecting ends of said optical fibers in a circular pattern centered about said opening to collect said back-scattered light, said housing of said optical fiber holder comprising a tubular portion adapted to engage a lens housing of a lens system adapted to focus said light beam at said interrogation zone, and thereby provide support for said optical fiber holder between said lens system and said particle-interrogation zone.

5. The back-scatter detector as defined by claim 4 wherein each optical fiber has a diameter of about 500 microns.

6. The back-scatter detector as defined by claim 4 wherein said fiber optic holder is designed to support a linear portion of each optical fiber in the vicinity of its light collecting end so that the respective axes of said supported linear portions of the optical fibers converge at or near the anticipated location of said interrogation zone.

7. The back-scatter detector as defined by claim 4 wherein said photodetector comprises a photomultiplier tube.

8. The back-scatter detector as defined by claim 4 wherein said fiber optic holder is designed to support a linear portion of each fiber in the vicinity of its light collecting end so that said light collecting end receives back-scattered light at a nominal angle of about 7 degrees, plus or minus 2 degrees.

* * * * *